(12) United States Patent
Tyvoll et al.

(10) Patent No.: US 10,196,604 B2
(45) Date of Patent: Feb. 5, 2019

(54) MITOCHONDRIAL INHIBITORS FOR USE IN CULTURING PLURIPOTENT STEM CELLS

(71) Applicants: The Board of Trustees of the Leland Stanford Junior University, Stanford, CA (US); BOARD OF REGENTS OF THE UNIVERSITY OF TEXAS SYSTEM, Austin, TX (US)

(72) Inventors: David Alvin Tyvoll, La Jolla, CA (US); Christopher S. Navara, San Antonio, TX (US); James P. Collman, Stanford, CA (US); Christopher Jeffrey Barile, San Carlos, CA (US)

(73) Assignees: The Board of Trustees of the Leland Stanford Junior University, Stanford, CA (US); Board of Regents of the University of Texas System, Austin, TX (US)

( * ) Notice: Subject to any disclaimer, the term of this patent is extended or adjusted under 35 U.S.C. 154(b) by 33 days.

(21) Appl. No.: 15/319,319

(22) PCT Filed: Jun. 19, 2015

(86) PCT No.: PCT/US2015/036787
§ 371 (c)(1),
(2) Date: Dec. 15, 2016

(87) PCT Pub. No.: WO2015/196139
PCT Pub. Date: Dec. 23, 2015

(65) Prior Publication Data
US 2017/0130198 A1    May 11, 2017

Related U.S. Application Data

(60) Provisional application No. 62/015,059, filed on Jun. 20, 2014.

(51) Int. Cl.
| | |
|---|---|
| *C12N 5/00* | (2006.01) |
| *C12N 5/0735* | (2010.01) |
| *C07D 257/06* | (2006.01) |
| *C07D 257/04* | (2006.01) |

(52) U.S. Cl.
CPC ......... *C12N 5/0606* (2013.01); *C07D 257/04* (2013.01); *C07D 257/06* (2013.01); *C12N 2500/02* (2013.01); *C12N 2500/30* (2013.01); *C12N 2501/999* (2013.01)

(58) Field of Classification Search
CPC ... C12N 5/0606; C07D 257/04; C07D 257/06
See application file for complete search history.

(56) References Cited

U.S. PATENT DOCUMENTS

| | | | |
|---|---|---|---|
| 8,012,751 B2 | 9/2011 | Thomson et al. | |
| 2010/0184033 A1* | 7/2010 | West | C12N 5/0606 435/6.16 |
| 2011/0301180 A1 | 12/2011 | Collman et al. | |
| 2013/0323833 A1 | 12/2013 | Zhu et al. | |

FOREIGN PATENT DOCUMENTS

| | | |
|---|---|---|
| WO | 2007007054 A1 | 1/2007 |
| WO | 2007030870 A1 | 3/2007 |
| WO | 2011142832 | 11/2011 |

OTHER PUBLICATIONS

Kielberg (2010) "Cryopreservation of Mammalian Cells—Protocols" Thermo Scientific; 14:1-2.
Rodriguez and Acosta (1996) "Inhibition of Mitochondrial Function in Isolated Rat Liver Mitochondria by Azole Antifungals" J. Biochem. Toxicology; 11(3):127-131.
Varum et al. (2009) "Enhancement of Human Embryonic Stem Cell Pluripotency Through Inhibition of the Mitochondrial Respiratory Chain" Stem Cell Res.; 3(2-3):142-156.
Xu et al. (2013) "Mitochondrial Regulation in Pluripotent Stem Cells" Cell Metabolism; 18:1-8.

* cited by examiner

*Primary Examiner* — Marcia S Noble
(74) *Attorney, Agent, or Firm* — Brian E. Davy; Bozicevic, Field & Francis LLP (57) ABSTRACT

Disclosed are certain heterocyclic organic compounds that inhibit mitochondrial respiration and also lead to the maintenance of pluripotency of human embryonic stem cells in culture, even in the presence of oxygen. Exemplified are compounds, such as substituted 5-aminotetrazoles, which are reversible mitochondrial inhibitors. The pluripotency of the stem cells after culture is verified by the overexpression of pluripotent stem cell markers, exemplified by at least one of the genes NANOG, OCT4, and SURVIVIN after periods of culture in ambient oxygen.

20 Claims, 2 Drawing Sheets
Specification includes a Sequence Listing.

MITOCHONDRIAL INHIBITORS FOR USE IN CULTURING PLURIPOTENT STEM CELLS

CROSS-REFERENCE TO RELATED APPLICATIONS

This application claims priority from U.S. Provisional Patent Application No. 62/015,059, filed Jun. 20, 2014, which is hereby incorporated by reference in its entirety, and is a U.S. national stage application of PCT/US2015/036787, having an international filing date of Jun. 19, 2015, the disclosure of which is hereby incorporated by reference in its entirety.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on Apr. 9, 2015, is named "3815_123_1PCT_seq_list_ST25.txt" and is 1004 bytes in size.

STATEMENT OF GOVERNMENT INTEREST

None.

BACKGROUND OF THE INVENTION

1. Field of the Invention

The invention is in the field of stem cell growth and the modulation and maintenance of stem cell pluripotency. Specifically, small molecule mitochondrial respiration inhibitors are provided for the growth and manipulation of pluripotent stem cells under ambient oxygen conditions.

2. Description of the Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

While the mechanisms underlying the maintenance of self-renewal and pluripotency are complex and poorly understood, there is evidence that culture conditions affect directly the growth and differentiation of stem cells. Ezashi et al. (Ezashi et al., 2005) demonstrated that culturing of human embryonic stem cells (i.e. hESCs) under low oxygen ($O_2$) tension (5%) reduced the appearance of spontaneous differentiation. This may be the normal physiological state, as early-stage mammalian embryos also develop under low $O_2$ concentrations (1.5%-5.3%) until they implant in the uterine endometrium, when $O_2$ levels increase with vascularization (Fischer and Bavister, 1993).

When cultured under low $O_2$ tension, mammalian cells decrease ATP production via oxidative phosphorylation in the mitochondria and increase glycolytic functions in order to meet energy demands. Studies of mitochondrial number and morphology in hESCs have demonstrated that undifferentiated hESCs have relatively few mitochondria in the cytoplasm and these mitochondria have few cristae, an indication of immature morphology (Cho et al., 2006; Oh et al., 2005; St John et al., 2005; Varum et al., 2011). As hESCs differentiate, the number of mitochondria with mature morphology increases, concomitant with the ATP levels produced by oxidative phosphorylation (Cho et al., 2006; Varum et al., 2011). Further maintenance of the pluripotent phenotype requires glycolysis (Zhou et al., 2012).

Moreover, it has previously been demonstrated that treatment with Antimycin A, an antibiotic isolated from *streptomyces* sp. which inhibits complex III of the mitochondrial respiratory chain, decreases ATP production via oxidative phosphorylation and simultaneously increases reactive oxygen species (ROS) formation in human embryonic stem cells. It also results in an increase in the expression of pluripotency factor NANOG and reduces differentiation (Varum et al., 2009). However, Antimycin A ([(2R,3S,6S,7R,8R)-3-[(3-formamido-2-hydroxybenzoyl)amino]-8-hexyl-2,6-dimethyl-4,9-dioxo-1,5-dioxonan-7-yl] 3-methylbutanoate) is known to be highly toxic (See U.S. Pat. No. 7,241,804) and accordingly undesirable for use in cell culture compositions that would contact human subjects.

US 20110301180, published Dec. 8, 2011, entitled "Reducing Platelet Activation, Aggregation and Platelet-Stimulated Thrombosis or Blood Coagulation by Reducing Mitochondrial Respiration," by Collman et al. discloses that inhibiting mitochondrial respiration in platelets reduces platelet activation or platelet aggregation. Some compounds used there for inhibiting platelet activation have been found to be useful in the methods disclosed here. However, the platelet activation involves different cellular pathways than those of pluripotent stem cell differentiation.

Additionally, pluripotent stem cells have been produced by expression of core transcription factors in somatic cells (Takahashi et al., 2007; Takahashi and Yamanaka, 2006) in a process called reprogramming resulting in induced pluripotent stem cells (iPS cells). These cells share many hallmarks with other pluripotent stem cells including preferential use of glycolytic pathways (Panopoulos et al., 2012; Varum et al., 2011).

It has also been demonstrated that inhibition of oxidative phosphorylation increases the efficiency of reprogramming to iPS cells (Son et al., 2013). In this study, Son et al. demonstrated that several inhibitors of oxidative phosphorylation were able to increase reprogramming efficiencies 10-20 fold and that there was demonstrated variability between inhibitors and their ability to affect reprogramming.

Mandal et al., "Mitochondrial function controls proliferation and early differentiation potential of embryonic stem cells," Stem Cells. 2011 March; 29(3):486-95 disclose that attenuating mitochondrial function during the first 7 days of differentiation results in normal repression of Oct4, Nanog, and Sox2. However, differentiation potential is compromised as revealed by abnormal transcription of multiple Hox genes. The authors attenuated mitochondrial function in (a) self-renewing and (b) differentiating mouse and human ESCs using a protonophore carbonyl cyanide m-chlorophenylhydrazone (CCCP).

Son et al. "Interference with the mitochondrial bioenergetics fuels reprogramming to pluripotency via facilitation of the glycolytic transition," Int J Biochem Cell Biol. 2013 November; 45(11):2512-8 discloses that disturbance of mitochondrial metabolism by canonical mitochondrial inhibitors enhances metabolic reprogramming toward a glycolytic state, enabling the highly efficient generation of induced pluripotent stem cells. The authors used the mitochondria inhibitors rotenone, TTFA, antimycin A, KCN, oligomycin A and FCCP. However, these inhibitors are toxic. Rotenone exposure has been linked to the development of Parkinson's disease in farm workers. Rotenone also has off target effects on the microtubule cytoskeleton in addition to blocking the transfer of electrons from complex 1 to ubiquinone. Antimycin A is used as a piscicide, and as little as 200 mg is a lethal dose of KCN in humans.

There remains an unmet need to be able to grow and manipulate pluripotent stem cells, particularly human pluripotent stem cells, conveniently under ambient oxygen conditions.

SUMMARY OF THE INVENTION

The following brief summary is not intended to include all features and aspects of the present invention, nor does it imply that the invention must include all features and aspects discussed in this summary.

The present invention comprises, in certain aspects, a method for maintaining pluripotent stem cells in culture and retaining or inducing pluripotency, comprising the step of culturing said stem cells in ambient oxygen conditions in the presence of a medium containing an azole compound that is an inhibitor of mitochondrial respiration. In certain aspects, the stem cells may be human pluripotent stem cells, including human embryonic stem cells.

The present invention comprises, in certain aspects, compositions and methods wherein the azole compound is present in the medium between 0.01 mM and 10 mM. The present invention comprises, in certain aspects, methods as described above wherein the substituted azole compound has the formula of Formula 1

Formula I wherein X is one of $CH_2$, O, NH or S; and R1 is H, a lower substituted alkyl group, or a substituted alkyl-aryl group, with the proviso that X cannot be $CH_2$ when R1 is H.

In a further embodiment, the present invention comprises culturing a pluripotent stem cell with a compound that is a mitochondrial inhibitor and is further one or more of a compound Compounds having at least a 1.5 fold change in expression of a stem cell marker, selected form Formula I or compound 3 5-[(3R or 3S)-dithiolan-3-yl]pentanoic acid (i.e. lipoic acid as a racemate); compound 4 (5-methylthiazole), compound 5 (3-methyl-4-phenyl-1H-imidazole-2-thione). as well as Formula I compound 6 (ethyl 2-(1H-tetrazol-5-yl)acetate), Formula I compound 7 (1H-tetrazol-5-amine) and Formula I compound 12 (5-methylsulfanyl-1H-tetrazole)

The compounds may be buffered with selected salts. These include sodium (especially) or other pharmaceutically acceptable salts, for example, inorganic salt with hydrochloric acid, sulfuric acid, nitric acid, phosphoric acid or hydrobromic acid; or organic salt with fumaric acid, maleic acid, acetic acid, malic acid, tartaric acid, citric acid, methanesulfonic acid or p-toluenesulfonic acid. These are useful if high concentrations of the azole compound(s) are used. High concentrations can be used because the present compounds are not toxic to cells or humans. Under high concentrations they may exceed the buffering capacity of the media.

The present invention comprises, in certain aspects, methods for culturing pluripotent stem cells under ambient oxygen conditions and maintaining pluripotency, in a cell culture medium comprising providing the cell culture medium with between 0.01 mM, or 0.1 mM and 10 mM of compound selected from the group consisting of 5-[(3R or 3S)-dithiolan-3-yl]pentanoic acid (compound 3), 5-methylthiazole (compound 4), 3-methyl-4-phenyl-1H-imidazole-2-thione (compound 5), ethyl 2-(1H-tetrazol-5-yl)acetate (compound 6), 5-aminotetrazole (compound 7) and 5-methylsulfanyl-1H-tetrazole (compound 12), or selected from the group consisting of compound 6 and compound 7, whereby said pluripotency is maintained during said culturing under ambient oxygen conditions.

The present invention comprises, in certain aspects methods as described above, wherein said culturing occurs under a condition comprising at least one of (a) greater than 72 hrs., (b) one cell doubling, or (c) 10 cell passages.

The present invention comprises, in certain aspects, methods such as described above, wherein the azole compound is at least one inhibitor selected from the group consisting of 5-[(3R or 3S)-dithiolan-3-yl]pentanoic acid (compound 3), 5-methylthiazole (compound 4), 3-methyl-4-phenyl-1H-imidazole-2-thione (compound 5), ethyl 2-(1H-tetrazol-5-yl)acetate (compound 6), 5-aminotetrazole (compound 7) and 5-methylsulfanyl-1H-tetrazole (compound 12).

The present invention comprises, in certain aspects, a method such as described above wherein the azole compound is a molecule selected from the group represented by Formula I above, further having a molecular weight of less than 300 Daltons.

The present invention comprises, in certain aspects, methods as described above wherein the stem cells are human cells selected from the group consisting of embryonic stem cells, modified hES cell lines, induced pluripotent stem (iPS) cell lines, and human progenitor cells.

The methods of the present invention may further comprise the measurement of cells in the culture for expression of at least one of the genes selected from the group consisting of NANOG, Octamer-binding protein 4 (OCT4), and SURVIVIN.

The present invention comprises, in certain aspects, methods for growing human embryonic stem cells (hESCs), pluripotent stem cells, or induced pluripotent stem cells, comprising:

(a). providing the cells with a cell growth media known for use in culturing stem cells, but supplemented with an azole compound that is an inhibitor of mitochondrial respiration (said azole compound further being one as defined above);

(b). culturing the cells on a feeder layer in a first culture medium in the presence of said cell growth media, under ambient oxygen conditions;

(c). splitting the cells into different cultures, removing any overtly differentiated colonies, and then passaging split cells into fresh cell growth media as recited in step (a); then (d). removing the media in step (c) from the culture and obtaining the human cells, wherein obtained human cells possess pluripotency.

The present invention comprises, in certain aspects, methods such as described above, further comprising the step of cryopreserving the cells after culture.

The present invention comprises, in certain aspects, compositions such as described above, including a composition of stem cell culture medium comprising a cell growth medium including growth factors, buffer, serum material, and an azole compound that is an inhibitor of mitochondrial respiration, wherein the stem cell culture medium maintains the pluripotency of a stem cell under ambient oxygen conditions. The present invention comprises, in certain aspects, compositions such as described above wherein the inhibition by the heterocyclic organic molecule is reversible. The present invention comprises, in certain aspects, compositions and methods such as described above, wherein the heterocyclic organic molecule induces the overexpression of at least one of the genes selected from the group consisting of NANOG, OCT4 and Survivin by at least 10%. The present invention comprises, in certain aspects, compositions such as described above wherein the molecular weight of the heterocyclic organic molecule is less than 250 Daltons.

The present invention also comprises, in certain aspects, kits for using methods and compounds such as described above.

In another embodiment, the response is expression of at least one of the genes selected from the group consisting of NANOG, OCT4 and Survivin with preferential selection for higher expression and/or multiple responding genes.

Another embodiment is directed to a composition of stem cell culture medium comprising an aqueous buffer solution and an effective amount of a mitochondrial respiration inhibitor, wherein the stem cell culture medium maintains the pluripotency of a stem cell under ambient oxygen conditions. In certain embodiments, the mitochondrial respiration inhibitor is an organic heterocyclic compound selected from the group consisting of 5-aminotetrazole, 5-[(3R or 3S)-dithiolan-3-yl]pentanoic acid, 5-methylthiazole, 3-methyl-4-phenyl-1H-imidazole-2-thione, ethyl 2-(1H-tetrazol-5-yl)acetate, 5-methylsulfanyl-1H-tetrazole, thiazole and tetrazole, or a combination thereof.

BRIEF DESCRIPTION OF THE DRAWINGS

The present invention is illustrated by way of example, and not by way of limitation, in the figures of the accompanying drawings.

DETAILED DESCRIPTION

As will be described below, the present invention provides a method and a composition for growing stem cells in a media containing certain non-toxic small molecules, while maintaining the pluripotency of stem cells in the culture, under ambient oxygen conditions.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, the term "about" is interpreted to mean plus or minus 5% of a stated numerical value.

The term "stem cell" is used herein according to common definition, in particular as an isolated cell that (i) is capable of renewing itself; and (ii) can give rise to more than one type of cell through asymmetric cell division. Stem cells typically give rise to a type of multipotent cell called a progenitor cell; progenitor cells, in turn, proliferate and differentiate into lineage-committed cells. Stem cells can be embryonic, or "nonembryonic", stem cells (i.e., are not isolated from embryo tissue). Stem cells are preferably of mammalian or primate origin and may be human or non-human in origin. The stem "pluripotent stem cells" refers, according to common definition, to cells capable of differentiating into one of many cell types. As stated at the web site of the California Stem Cell Agency, so-called pluripotent cells, which have the ability to form all cells in the body, can be either embryonic or induced pluripotent stem (iPS) cells. All stem cells, whether they are tissue stem cells or pluripotent cells, have the ability to divide and create an identical copy of themselves. This process is called self-renewal. The cells can also divide to form cells that go on to develop into mature tissue types such as liver, lungs, brain, or skin.

The term "modified hES cell lines" refers to cells such as those obtained from WiCell, that have been genetically modified, and are further exemplified (for example) in the H9 hOCT4-pGZ, Oct4 reporter line that expresses GFP only when the Oct4 promoter is active. GFP downregulates upon cellular differentiation. OCT4/GFP positive cells are selectable using Zeocin. The definition further includes any genetically modified stem cell, e.g as described in "Human embryonic stem cells genetically modified to contain a nucleic acid and cultured with fibroblast growth factor," U.S. Pat. No. 8,637,311.

As used herein, the term "placental stem cell" refers to a stem cell or progenitor cell that is derived from a mammalian placenta, regardless of morphology, cell surface markers, or the number of passages after a primary culture. The term "placental stem cell" as used herein does not, however, refer to a trophoblast. A cell is considered a "stem cell" if the cell retains at least one attribute of a stem cell, e.g., a marker or gene expression profile associated with one or more types of stem cells; the ability to replicate at least 10-40 times in culture, the ability to differentiate into cells of all three germ layers; the lack of adult (i.e., differentiated) cell characteristics, or the like. The terms "placental stem cell" and "placenta-derived stem cell" may be used interchangeably, as described further in "Placental stem cell populations," U.S. Pat. No. 8,057,788.

The term "embryonic stem cell (ES cell)" means an undifferentiated cell derived from an embryo, which has the capability of differentiating into all of the mature tissues of the body. Here, "embryo" means a fertilized egg up to eight (8) weeks after its fertilization or a nucleus-transferred oocyte in the corresponding developmental stage. An embryo is created by a repetitive division of such fertilized egg or nucleus-transferred oocyte, and comprises a blastocyst containing an inner cell mass (ICM) and an outer trophectoderm.

The term "induced pluripotent cell line" refers to stem cells obtained from induced pluripotent stem cells by way of reprogramming of somatic cells (iPS cells), described e.g. in "Method for producing induced pluripotent stem cells," US 20130065243 and further described below.

By the term "maintains pluripotency" is meant preventing or minimizing the amount of cell differentiation, e.g., spontaneous differentiation in culture. In certain embodiments, such as, e.g., when culturing stem or progenitor cells, the term also includes maintaining the immature state which increases the ability of the stem cell to differentiate into one or more mature, differentiated cell lineages.

The term "NANOG" refers to a transcription factor involved with self-renewal of undifferentiated embryonic stem cells. In humans, this protein is encoded by the NANOG gene. Human NANOG protein is a 305 amino acid protein with a conserved homeodomain motif that is localized to the nuclear compartment of cells. NANOG is thought to function in concert with other factors such as POU5F1 (OCT4) and SOX2 to establish ESC identity. The term further refers to NANOG Nanog homeobox [*Homo sapiens* (human)], Entrez Gene ID: 79923 (official symbol NANOG), its genomic regions, transcripts, and products, GenBank: AB093576.1, and NANOG, NM_024865.2 (mRNA). The term may also, if the context provides, refer to mouse Entrez 71950.

The term "OCT4" refers to OCT4 (octamer-binding transcription factor 4), also known as POU5F1 (POU domain, class 5, transcription factor 1), and is a protein that in humans is encoded by the HGNC gene symbol POU5F1. It is Entrez Gene ID 5460. The nucleic acid sequence may be found at GenBank: Z11898.1. The amino acid sequence may be found at the "FASTA" tab. Various sequence variants can be found at NCBI Protein database under "POU domain." OCT 4 is also represented by OCT4, NM_002701.4 (mRNA).

The term "SOX2" refers to an intronless gene that encodes a member of the SRY-related HMG-box (SOX) family of transcription factors involved in the regulation of embryonic development and in the determination of cell fate. The official gene symbol is SOX2; the entrez gene ID is 6657, SOX2 SRY (sex determining region Y)-box 2 [*Homo sapiens* (human)]; amino acid sequences may be found at NCBI protein data base under SOX2; a sample sequence is at GenBank: AAH13923.1. SOX2 is also represented in SOX2, NM_003106.3 (mRNA) and represents a potential marker for pluripotency in the present methods.

The term "SURVIVIN" refers to a member of the family of inhibitor of apoptosis proteins, and functions as a key regulator of mitosis and programmed cell death, as described e.g. in Mita et al., "Survivin: Key Regulator of Mitosis and Apoptosis and Novel Target for Cancer Therapeutics," Clin Cancer Res Aug. 15, 2008; 14:5000. Survivin is further described in US 20110091489, "Survivin Peptide Vaccine." Sequences of appropriate sequences are given in Conway et al., "Three differentially expressed survivin cDNA variants encode proteins with distinct antiapoptotic functions," BLOOD, 95:1435-1442 (2000).

As used herein, an agent that is involved in "retaining or inducing pluripotency" can either enable a stem cell culture to retain its pluripotency or facilitate the induction of a pluripotent state, i.e. aid the creation of an induced pluripotent stem cell. Evidence of such activity may be also shown in a compound that modulates or maintains the pluripotency of a stem cell as evidenced by at least a 10% increase of expression of at least one of the genes which are characteristic of pluripotency of a stem cell, including but not limited to NANOG, OCT4, and SURVIVIN.

By "mitochondrial inhibitor" is meant a compound that significantly reduces mitochondrial respiration, by reducing mitochondrial oxygen consumption of a cell. Such inhibition may be determined by a number of assays. For example, mitochondria isolated from liver of tilapia (*Sarotheridon mossambica*) are incubated in the appropriate concentration of HC for 2 minutes at 0° C. The suspension of mitochondria and the HC are the injected into a respiration chamber, and the respirometer is allowed to stabilize for 1 minute before data collection. The mitochondrial respiration rate is measured at different concentrations for each HC. The percentage of mitochondrial inhibition is determined by comparing these rates to the respiration rate in the absence of the HC. Mitochondrial inhibition is presented in IC50. A weak inhibitor may still be a useful inhibitor, provided it is given at a high enough concentration (a large IC50 value).

As used herein, "effective amount" is meant a quantity of an active agent or a period of time, which produces a desired effect. The term mM has the standard meaning of 1 millimolar, where 1 mol/L=1 mol/dm$^3$=1 mol dm$^{-3}$=1 M=1000 mol/m$^3$.

As used herein, "ambient oxygen conditions" or "ambient $O_2$ pressure" refers to conditions where cells in culture are not artificially controlled to reduce exposure to oxygen in the environment. Ambient oxygen conditions exist in the mixture of gases that form the earth's atmosphere. At sea level dry air has a density of 1.226 kilograms per cubic metre and consists of 78.08 percent nitrogen, 20.95 percent oxygen, 0.93 percent argon, 0.03 percent carbon dioxide, with smaller quantities of ozone and inert gases; water vapor varies between 0 and 4 percent and in industrial areas sulphur gases may be present as pollutants. The percentage of oxygen at 20.95 percent may be regarded as variable under various cell culture conditions, e.g. from 10% to 30%. For details, see Mohyeldin et al, "Oxygen in Stem Cell Biology: A Critical Component of the Stem Cell Niche," Cell Stem Cell Volume 7, Issue 2, p150-161, 6 Aug. 2010. Ambient oxygen conditions may be further understood by contrast to culture and cell handling conditions done in an artificial atmospheric environment having little or no oxygen.

The term "lower substituted alkyl group" means groups as exemplified here in "R," and may include alkyl groups of 2-20 carbon chains, substituted within said chains by non-carbon atoms including O (alkoxy), S, N, or aryl groups. Possible alkyl groups are straight or branched $C_{1-10}$ alkyl group (e.g. methyl, ethyl, propyl, butyl, pentyl, isopropyl, isobutyl, 1-methylpropyl, 3-methylbutyl or hexyl), $C_{3-7}$ cycloalkyl group (e.g. cyclopropyl, cyclopentyl, cyclohexyl or cycloheptyl), and alkyl-substituted $C_{3-7}$ cycloalkyl group, preferably straight or branched $C_{1-6}$ alkyl group (e.g. methyl, ethyl, propyl, butyl or pentyl), and $C_{5-7}$ cycloalkyl group (e.g. cyclopentyl or cyclohexyl). Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Accordingly, the term "lower alkoxy" means an alkyl group having 2-20 carbon chains, substituted with pendant or internal oxygen atoms.

The term "substituted alkyl-aryl group" means a substituted alkyl group or a substituted aryl group, and includes alkyl groups such as possible alkyl groups listed above and a linear or branched chain including both alkyl groups as defined above and aryl groups, which may be heteroaryl. Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl. Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" or "hetero-aromatic" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

In this connection, "heterocyclic compounds" are neutral or charged organic molecules, constituting covalently bonded cycles that have 3-10 atoms, at least one of which is a heteroatom. Heteroatoms typically include nitrogen, oxygen, sulfur, phosphorus and selenium. In one embodiment, the cycle comprises 5-6 atoms including at least two atoms that are heteroatoms. In other embodiments the heteroatoms are separated from one another by one atom in the cycle. In certain embodiments the heterocyclic compounds have two heteroatoms that are each capable of binding to metal ion centers. In some embodiments the heterocyclic compounds have one or more substituent groups, such as polar groups that modulate the water-solubility of the heterocyclic compound.

Unless otherwise indicated, the term "heteroarylalkyl" or "heteroaryl-alkyl" means a heteroaryl moiety bound to an alkyl moiety.

General Methods

Applicants have discovered that certain small heterocyclic organic molecules, when present in a culture medium, maintained the pluripotency of stem cells, including human embryonic stem cells. These heterocyclic organic molecules are also mitochondrial inhibitors, and the inhibition by the molecules may be reversible.

In one embodiment, specific heterocyclic organic compounds have been identified to induce overexpression of transcription factors used for inducing human pluripotent stem cells, including NANOG, OCT4, and overexpression of SURVIVIN (an inhibitor of apoptosis), which has been linked to pluripotency (Mull et al., 2014), by at least 10% in the in vitro assay. As described herein, the compounds (exemplified in Table 1), which are heterocyclic five-membered ring-based compounds, can achieve at least 10% overexpression when compared with the control (increases shown in Table 2). The active agents include 5-[(3R or 3S)-dithiolan-3-yl]pentanoic acid (3), 5-methylthiazole (4), 3-methyl-4-phenyl-1H-imidazole-2-thione (5), ethyl 2-(1H-tetrazol-5-yl)acetate (6), 5-aminotetrazole (7) and 5-methylsulfanyl-1H-tetrazole (12).

Preferably, the active agent is a 5-substituted tetrazole small molecule of formula I. Active agents 6, 7 and 12 are 5-substituted tetrazole small molecules. The substitution at the 5-position of tetrazoles includes but is not limited to amino, sulfanyl and alkyl groups as shown in Formula I:

Formula I wherein X is one of $CH_2$, O, NH or S; and R1 is H, a lower substituted alkyl group, or a substituted alkyl-aryl group, with the proviso that X cannot be $CH_2$ when R1 is H. Because the core pluripotency transcription factors (OCT4 and NANOG) are co-regulated, an increase of expression in any one of these genes will likely lead to an increase of expression in the other two over time. Therefore, an overexpression in any one of the markers OCT4, SURVIVIN and NANOG is indicative of the positive effect of an agent on the maintenance of pluripotency of the stem cells.

Preferably, the active agent for the maintenance of pluripotency of stem cells is also a mitochondrial inhibitor. More preferably, the active agent is a reversible mitochondrial inhibitor. As shown in Table 2, compounds 4, 7 and 12 are the three reversible mitochondrial inhibitors in the table and are all positive as an agent for the maintenance of pluripotency of stem cells. A reversible inhibitor will allow the stem cell to be rid of the agent when it is required.

Preferably, the molecular weight of the agent is less than 300 Daltons, or less than 250 Daltons, less than 150 Daltons, or less than 120 Daltons. The three compounds 4, 7 and 12, as discussed above, have molecular weights of only 116 or less. Without being bound by theory, the relatively small size of these molecules may be conducive to fitting into the active size of an enzyme, such as cytochrome c oxidase.

Figure 1A:
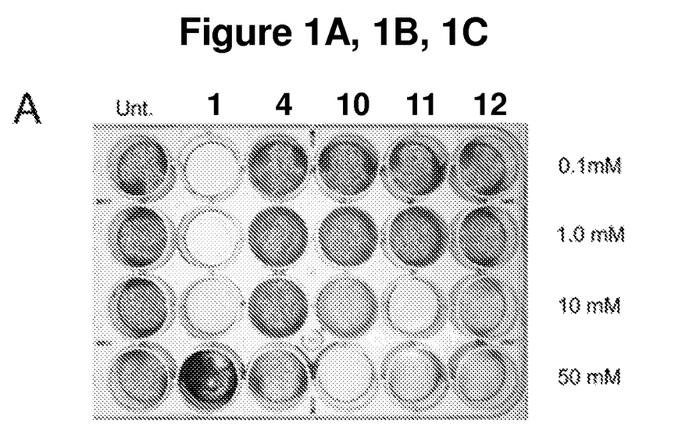
FIGS. 1A, 1B, and 1C is a series of photographs showing the results of toxicity testing of mitochondrial inhibitors on human embryonic stem cells.

FIG. 1A shows the toxicity testing results for compounds 1, 4, 10, 11 and 12. Compound 1 was toxic at the initially tested concentration. Compound 4 demonstrated no toxicity to 10 mM, while compounds 10, 11, 12 were nontoxic to 1 mM.

Figure 1B:
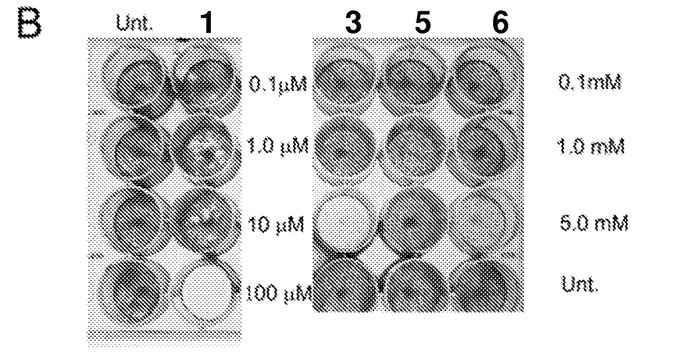

FIG. 1B includes compounds 1, 3, 5 and 6. The concentration for the retested compound 1 is in a lower range of 0.1 to 100 μM than in FIG. 1A. It is shown to be nontoxic up to 10 μM. Compounds 3 and 6 were nontoxic to 1 mM, while compound 5 was nontoxic to at least 5 mM.

Figure 1C:
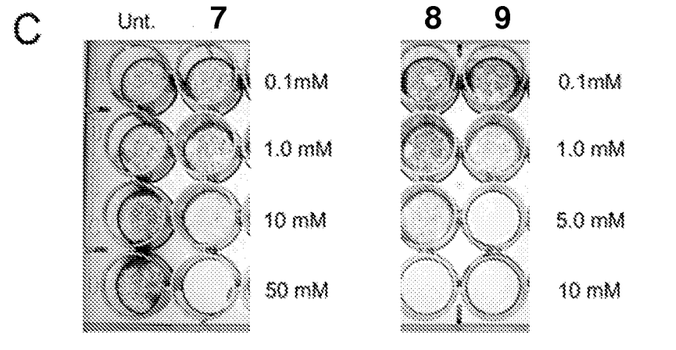

FIG. 1C shows the toxicity test results for compounds 7, 8 and 9. Compounds 7 and 8 were nontoxic to 1 mM. Compound 9 was nontoxic up to 0.1 mM and had minimal toxicity at 1 mM.

All compounds in Table 1 except 1, 2 and 9 showed no toxicity at concentrations up to 1 mM (see FIGS. 1A, 1B, 1C). Compound 9 had minimal toxicity at 1 mM. Compound 1 was toxic at all concentrations tested initially (FIG. 1A) so it was retested at concentrations 1000-fold less concentrated and found to be well tolerated up to 10 μM. Compound 2 was not soluble in the culture media and was not tested further.

Figure 2:
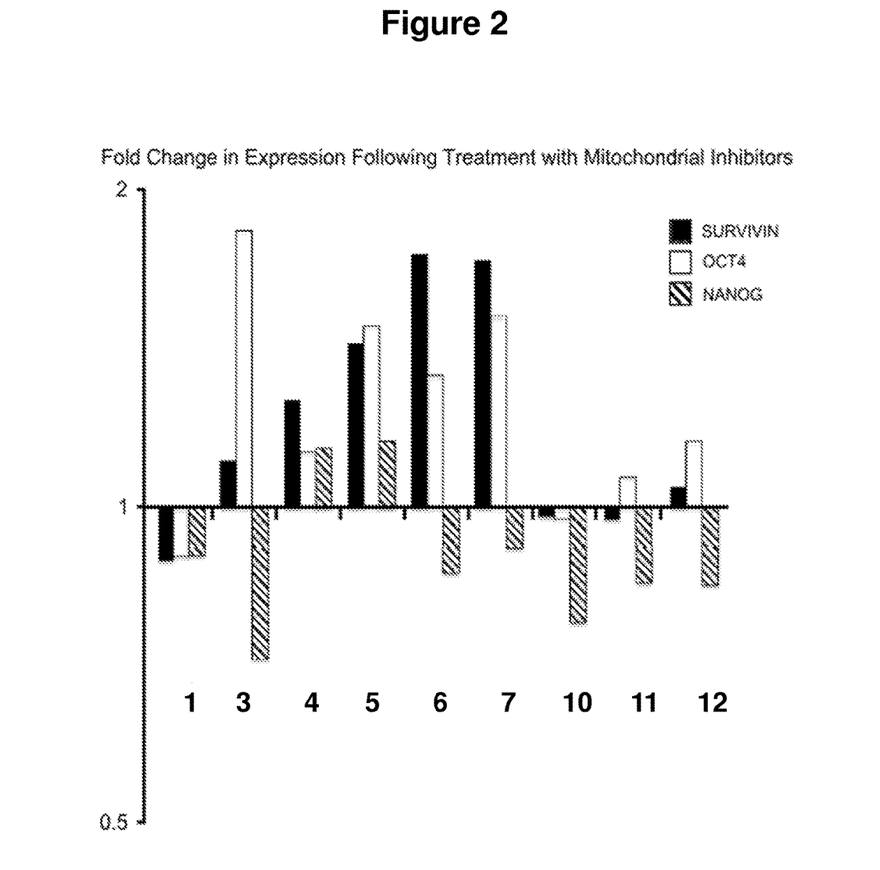
FIG. 2 is a graph that shows the Quantitative Reverse Transcriptase PCR (qRT-PCR) analysis of gene expression for SURVIVIN, OCT4 and NANOG in the presence of compounds numbered as in Table 1.

FIG. 2 shows the Quantitative Reverse Transcriptase PCR (qRT-PCR) analysis of gene expression for SURVIVIN, OCT4 and NANOG in the presence of a mitochondrial inhibitor. Increased expression of the probed genes is shown as bars above the X-axis at 1, while decreased expression has bars below the X-axis. As is shown in FIG. 2, two compounds (4 and 5) resulted in increased expression of all three genes following treatment. Four other compounds (3, 6, 7 and 12) resulted in increased expression of SURVIVIN and OCT4 but not NANOG. The remaining three compounds either resulted in decreased expression of all three genes (1 and 10) or only resulted in an increase in OCT4 and no other genes (11).

Table 2 further shows that 5-methylthiazole (4), 5-aminotetrazole (7) and 5-methylsulfanyl-1H-tetrazole (12) were reversible mitochondrial inhibitors. A value of above 1 in the "Expression relative to control" column means that the particular gene is overexpressed. All the above three compounds, 4, 7 and 12, caused overexpression of at least one of the probed genes by at least 10%. Therefore, they qualify as agents for maintenance of the pluripotency of stem cells.

Thus, inhibition of mitochondrial oxidative phosphorylation provides a novel tool for both the maintenance of pluripotent stem cells and also increasing the efficiency of reprogramming. Table 2 shows that these inhibitors are able to modulate the expression of the pluripotency transcription factors OCT4 and NANOG.

It has recently been shown that the oncofetal protein SURVIVIN is also important in the maintenance of pluripotency as inhibition of mRNA expression resulted in differentiation (Mull et al., 2014). Therefore, Table 2 further includes the effects of these compounds on SURVIVIN gene expression in human embryonic stem cells. As shown in Table 2, compounds 3, 4, 5, 6, 7 all have SURVIVIN overexpression by at least 10%.

In one embodiment, a marker for the pluripotent stems cells includes at least one selected from the group consisting of NANOG, Octamer-binding protein 4 (OCT4), sex determining region Y-box 2 (SOX2), ATP-binding cassette, sub-family G, member 2 (ABCG2), crypto, forkhead box D3 (FoxD3), Connexin43, Connexin45, human telomerase reverse transcriptase (hTERT), undifferentiated embryonic cell transcription factor 1 (UTF-1), zinc finger protein 42 (ZFP42), stage-specific embryonic antigen 3 (SSEA-3), stage-specific embryonic antigen 4(SSEA-4), tumor-related antigen-1-60 (TRA1-60), and tumor-related antigen-1-81 (TRA1-81).

Preferably, an active agent causes increased expression of one of the genes selected from the group consisting of NANOG, Octamer-binding protein 4 (OCT4), and SURVIVIN, including overexpression resulting in an increase of at least 10% in addition to the overexpression of SURVIVIN also by at least 10%.

More preferably, the active agent induces overexpression of one of the genes selected from the group consisting of NANOG, Octamer-binding protein 4 (OCT4), by at least 30% in addition to the overexpression of SURVIVIN also by at least 30%.

Most preferably, the active agent causes overexpression of one of the genes selected from the group consisting of NANOG, Octamer-binding protein 4 (OCT4), by at least 50% in addition to the overexpression of SURVIVIN also by at least 50%. Compound 7 (i.e. 5-aminotetrazole) of Table 2 overexpressed both OCT4 and SURVIVIN by at least 50%.

Applicable Stem Cells

The present media and methods are applicable to a variety of stem cell types. A preferred cell type is a human embryonic stem cell (ES cell). The characteristic features of human pluripotent ES cells developed by Thomson et al. in 1998 (Thomson et al., Science, 282:1145-1147 (1998)) are as follows: (1) expression of stage-specific embryonic antigen-3 (SSEA-3), stage-specific embryonic antigen-4 (SSEA-4), tumor rejection antigen 1-60 (TRA-1-60), tumor rejection antigen 1-81 (TRA-1-81), and alkaline phosphatase; (2) high telomerase activity; and (3) differentiation into cells from all three germ layers when injected into mice.

Other undifferentiated cells encompassed by the present invention will also express similar and/or different markers characteristic of the undifferentiated state and/or of a differentiated state of the cell. The expression of such markers may be analyzed to determine whether the pluripotency of a stem cell is maintained. In other embodiments of the present invention, markers for the pluripotent stems cells include ATP-binding cassette, sub-family G, member 2 (ABCG2), crypto, forkhead box D3 (FoxD3), Connexin43, Connexin45, human telomerase reverse transcriptase (hTERT), undifferentiated embryonic cell transcription factor 1 (UTF-1), zinc finger protein 42 (ZFP42), stage-specific embryonic antigen 3 (SSEA-3), stage-specific embryonic antigen 4 (SSEA-4), tumor-related antigen-1-60 (TRA1-60), and tumor-related antigen-1-81 (TRA1-81).

Formulations and Culture Conditions

The present methods are applicable to a variety of culture media and culture steps. They are primarily directed to human stem cells, which are known to be difficult to culture, compared to animal stem cells. As described in the example below, the stem cells of interest may be cultured with inactivated mouse embryonic fibroblasts (MEFs). MEFs continue to be the most commonly used feeder cell type for the culture and maintenance of mouse and human derived ESC lines. MEFs provide a complex, but unknown mixture of nutrients and substrata for the long term growth and proliferation of undifferentiated pluripotent ESCs. Other feeder cells are known and applicable to the present methods, e.g. JK1 feeder cells, or SNL 76/7 feeder cells.

Applicable materials and methods can be found, e.g. in Schwarts et al., "Traditional human embryonic stem cell culture," Methods Mol Biol. 2011; 767:107-23, which describes specific reagents, e.g. Dulbecco's modified Eagle medium: Ham's F12 (DMEM/F12+GlutaMAX, Invitrogen, #10565), Dulbecco's phosphate buffered saline (DPBS--) without Mg2+ and Ca2+, Dulbecco's phosphate buffered saline (DPBS++) with Mg2+ and Ca2+, KnockOut™ Serum Replacement (KSR) (Invitrogen, #108280-028), 2-Mercaptoethanol, 55 mM (1,000×) in PBS (such as Invitrogen, #21985-023), GlutaMax (100×) (Invitrogen, #35050), Human basic fibroblast growth factor (bFGF) (Stemgent, #03-0002), MEM-Nonessential amino acids (NEAA) 100x (10 mM) (Hyclone, #SH30238.01), Hybri-Max dimethyl sulfoxide (Sigma-Aldrich, #D2650), Water for embryo transfer (Sigma, #W1503, Fetal bovine serum (FBS) (Hyclone, #SH30070.03), Pen-strep 100× (optional) (Invitrogen, #15070-063), TrypLE-Express (Invitrogen, #12604), Collagenase IV (20,000 U, Invitrogen, #17104-019), CF-1 mouse embryonic fibroblasts (ATCC, #SCRC-1040), Nikon Object Marker, catalog # MBW10020 (optional), 6-Well vacuum gas plasma-treated tissue culture dishes (such as BD Falcon, #353046), Sterile nylon membrane syringe filter (Pall Life Sciences, #PN 4433), Nalgene freezing container (containing isopropanol), 20 µL pipette tips (Eppendorf and others), 150 mm Tissue culture dishes (TPP, #93150), media and stock solutions including Human Basic FGF (bFGF) (10 µg/mL, 1 mL), Collagenase IV (200 U/mL, 100 mL), KnockOut™ Serum Replacement, MEF Medium (500 mL), Human PSC Medium (100 mL), Human PSC Cryopreservation Medium (10 mL, 2×). Methods include Preparation of Feeder Cell Stocks, Preparation of a Feeder Layer, Thawing Cryopreserved PSCs, Passaging PSCs, Collagenase Dissociation, and Cryopreservation.

Other applicable culture details may be found, e.g. in US 20130295579, "Method for preparing induced pluripotent stem cells and medium used for preparing induced pluripotent stem cells," published Nov. 7, 2013. As is known, these culture conditions involve induced pluripotent stem (iPS) cells, with characteristics similar to embryonic stem cells, prepared by overexpressing four transcription factors (Oct4, Sox2, Klf4 and c-Myc).

Further details on culture of non-human embryonic stem cells may be found in Navara, C. S., Redinger, C., Mich-Basso, J., Oliver, S, Ben-Yehudah, A., Castro, C., Simerly, C. (2007) Derivation and Characterization of Non-Human Primate Embryonic Stem Cells, Current Protocols in Stem Cell Biology (John Wiley and Sons). The present methods may be applicable to a variety of primate stem cells, including, without limitation, baboon stem cells. See, e.g. Paik, "Method of producing stem cell lines," US 20040043482, which describes stem cell lines established from baboon blastocyst.

Takahashi et al., "Induction of Pluripotent Stem Cells from Adult Human Fibroblasts by Defined Factors," Cell. 2007 Nov. 30; 131(5):861-72 discloses further culture media and methods that may be adapted for use with the present azole compounds and non-low $O_2$ conditions.

A further example of detailed culture conditions is given in Ulloa-Montoya et al., "Culture Systems for Pluripotent Stem Cells," Journal of Bioscience and Bioengineering, Vol. 100 (2005) No. 1 P 12-27. As disclosed there, pluripotent stem cells have the capacity to self-renew and to differentiate to cells of the three somatic germ layers that comprise an organism. While expanding stem cells in culture, it is critical to maintain their self-renewal and differentiation capacity. Culture of hematopoietic stem cells, mesenchymal stem cells, and pluripotent bone marrow derived adult stem cells is discussed, and these can be cultured according to the present methods.

Culturing Kits

Any of the compositions described herein may be comprised in a kit. In a non-limiting example, an active agent is included in a kit. The kit may further include water and buffer. The components of the kits may be packaged either in aqueous media or in lyophilized form. The container means of the kits will generally include at least one vial, test tube, flask, bottle, or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the agents, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that preserve or maintain the agonists or that protect against their degradation. Such kits generally will comprise, in suitable means, distinct containers for each individual reagent or solution. A kit will also include instructions for employing the kit components as well the use of any other reagent not included in the kit. Instructions may include variations that can be implemented.

Materials and Methods

Cell Culture

Human ES cells, WA09 (WiCell Research Institute, Madison, Wis.) were cultured on dishes coated for at least two hours with Matrigel (BD Biosciences, Franklin Lakes, N.J.). hES cell media containing 80% knockout Dulbecco's modified eagle medium (DMEM), 20% knockout serum replacer, 1% nonessential amino acids, 1% penicillin/streptomycin (100 U per 100 μg/ml), 2 mM L-glutamine, (all from Invitrogen, Carlsbad, Calif.) and 4 ng/ml basic fibroblast growth factor (bFGF, ReproCELL, San Jose, Calif.) was pre-conditioned by culture with inactivated mouse embryonic fibroblasts (MEF; Millipore, Billerica, Mass.) and collected every two days. hES cell lines were cultured with human conditioned media (HuCM) supplemented with 4 ng/ml bFGF and a heterocyclic compound of a certain concentration. hES cells were maintained by weekly manual passaging or bulk passaging using 1 mg/ml Collagenase IV (Invitrogen). hES cells were plated for experiments using Accutase (Fisher, Pittsburgh, Pa.) and plated at a density of 26,000 cells/cm$^2$.

Real Time Polymerase Chain Reaction

Total cellular RNA was extracted from cells using TRIzol (Invitrogen) and DNase treated with the DNA-free kit (Ambion, Austin, Tex., http (colon slash slash) www (dot) ambion.com) following manufacturer's directions for stringent conditions. RNA was dialyzed for 30 minutes against milliqwater, 10 mM Tris and 1 mM EDTA adjusted to pH 7.5 with HCL (all from Fisher). cDNA was synthesized using GeneAmp RNA PCR kit from Applied Biosciences (Fisher) and no-RT reactions were performed without reverse transcriptase and RNase inhibitor enzymes. One microgram of RNA was used, following manufacturer's directions. Quantitative real time polymerase chain reaction (qPCR) was performed to determine relative mRNA expression levels. Expression fold changes were calculated using the ΔΔCt method and normalized using the housekeeping gene, β-ACTIN as an internal control. Taqman master mix and gene assays with water only were used as a negative control. mRNA expression assays were analyzed in a triplicate PCR reaction with no-RT negative controls and each experiment was performed at least three independent times. Primers for OCT4 and NANOG were selected from predeveloped Applied Biosystems TaqMan Assays, which are pre-designed qPCR primers and TaqMan MGB probes; Oct-4 (Hs01895061_u1) and Nanog (Hs02387400_g1) were selected. Primers for SURVIVIN were:

```
forward
                                      (SEQ ID NO: 1)
5'-CGAGGCTGGCTTCATCCA-3', reverse
                                      (SEQ ID NO: 2)
5'-GCAACCGGACGAATGCTTT-3'
and the probe was
                                      (SEQ ID NO: 3)
5'-ACCCCATAGAGGAACATA-3'.
```

Toxicity Testing hES cells were plated as above and subjected to increasing concentrations of the mitochondrial inhibitors for 72 hr of culture. After 72 hr the cells were fixed in 2.0% formaldehyde and stained for 30 min with 0.05% crystal violet in distilled water. Stained cells were rinsed twice with distilled water and imaged using bright field microscopy.

EXAMPLES

Example 1

A batch of twelve mitochondrial inhibitors (i.e. compounds 1-12 of Table 1) was first tested for toxicity against human embryonic stem cells. These compounds were initially tested at concentrations from 0.1 mM to 50 mM. Only compound 1 needed to be retested at lower concentrations of 0.1 to 100 μM, outside the initial range.

TABLE 1

Compounds studied

| Compound | Molecular structure | Nomenclature |
|---|---|---|
| 1 | [structure] | [2-[2-(4-methylthiazol-5-yl)ethoxy]-2-oxo-ethyl]-triphenyl-phosphonium bromide |
| 2 | [structure] | 5-benzylsulfanyl-1H-tetrazole |
| 3 | [structure] | 5-[(3R or 3S)-dithiolan-3-yl]pentanoic acid (i.e. lipoic acid as a racemate) |
| 4 | [structure] | 5-methylthiazole |
| 5 | [structure] | 3-methyl-4-phenyl-1H-imidazole-2-thione (i.e. 5-phenylmethimazole) |
| 6 | [structure] | ethyl 2-(1H-tetrazol-5-yl)acetate |

TABLE 1-continued

Compounds studied

| Compound | Molecular structure | Nomenclature |
|---|---|---|
| 7 | [structure] | 1H-tetrazol-5-amine (i.e. 5-aminotetrazole) |
| 8 | [structure] | diethyl 1H-triazole-4,5-dicarboxylate |
| 9 | [structure] | 4,5-dibromo-1H-triazole |
| 10 | [structure] | 5-methyl-1H-tetrazole (comparative example) |
| 11 | [structure] | 2-(1H-tetrazol-5-yl)acetic acid |
| 12 | [structure] | 5-methylsulfanyl-1H-tetrazole |

Example 2

Based on the toxicity results, nine of the above twelve compounds in Example 1 were selected for further screening to assess their effects on the expression of OCT4, NANOG and SURVIVIN in human embryonic stem cells. The results are summarized in Table 2, along with the mitochondrial inhibition activities for these compounds which were disclosed in US20110301180A1 to Collman et al. the content of which has been incorporated herein by reference.

The pluripotency of these cultured human embryonic stem cells were characterized by the marker gene expression as analyzed by Quantitative Reverse Transcriptase PCR (qRT-PCR). All compounds were tested at 1 mM concentration for 72 hours except for compound 1 which was tested at 10 μM. The results of the analysis are compiled in Table 2. The reversibility of mitochondrial inhibition is presented in the right column.

TABLE 2

| Compound | Gene | Expression relative to control | One of the genes overexpressed by at least 10% | Inhibition/Reversibility in mitochondrial inhibition |
|---|---|---|---|---|
| 1 | SURVIVIN | 0.892 | No | No |
|  | OCT4 | 0.900 |  |  |
|  | NANOG | 0.902 |  |  |
| 3 | SURVIVIN | 1.110 | Yes | N/A |
|  | OCT4 | 1.846 |  |  |
|  | NANOG | 0.717 |  |  |
| 4 | SURVIVIN | 1.269 | Yes | Yes |
|  | OCT4 | 1.134 |  |  |
|  | NANOG | 1.141 |  |  |
| 5 | SURVIVIN | 1.438 | Yes | N/A |
|  | OCT4 | 1.496 |  |  |
|  | NANOG | 1.159 |  |  |
| 6 | SURVIVIN | 1.753 | Yes | N/A |
|  | OCT4 | 1.341 |  |  |
|  | NANOG | 0.867 |  |  |
| 7 | SURVIVIN | 1.731 | Yes | Yes |
|  | OCT4 | 1.532 |  |  |
|  | NANOG | 0.917 |  |  |
| 10 | SURVIVIN | 0.981 | No | N/A |
|  | OCT4 | 0.977 |  |  |
|  | NANOG | 0.778 |  |  |
| 11 | SURVIVIN | 0.975 | No | N/A |
|  | OCT4 | 1.072 |  |  |
|  | NANOG | 0.849 |  |  |
| 12 | SURVIVIN | 1.048 | Yes | Yes |
|  | OCT4 | 1.159 |  |  |
|  | NANOG | 0.844 |  |  |

Compounds as discussed herein have been shown to inhibit mitochondrial in the above referenced US 2011030180. The table below gives values for selected compounds useful in the present invention:

TABLE 3

| mitochondrial inhibition | |
|---|---|
| Compound No. | $IC_{50}$ (mg/ml) |
| 4 (94 in '825) | 23.5 |
| 12 (83 in '825) | 14.5 |
| 6 (80 in '825) | 100 |
| 5 (91 in '825) | 5.4 |
| 3 (90 in '825) | 37.1 |
| 1 (49 in '825) | 8.8 |
| 7 (34 in '825) | 8.5 |

The $IC_{50}$ show the reduction of mitochondrial respiration, i.e. reducing mitochondrial oxygen consumption; without wishing to be held to any scientific theory, it is suggested that the present compounds maintain a pluripotent state by inhibiting mitochondrial respiration in cells affected by these compounds.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

Cho, Y. M., S. Kwon, Y. K. Pak, H. W. Seol, Y. M. Choi, J. Park do, K. S. Park, and H. K. Lee. 2006. Dynamic changes in mitochondrial biogenesis and antioxidant enzymes during the spontaneous differentiation of human embryonic stem cells. Biochem Biophys Res Commun. 348:1472-8.

Ezashi, T., P. Das, and R. M. Roberts. 2005. Low 02 tensions and the prevention of differentiation of hES cells. Proc Natl Acad Sci USA. 102:4783-8.

Fischer, B., and B. D. Bavister. 1993. Oxygen tension in the oviduct and uterus of rhesus monkeys, hamsters and rabbits. J Reprod Feral. 99:673-9.

Mull, A. N., A. Klar, and C. S. Navara. 2014. Differential localization and high expression of SURVIVIN splice variants in human embryonic stem cells but not in differentiated cells implicate a role for SURVIVIN in pluripotency. Stem Cell Res. 12:539-549.

Oh, S. K., H. S. Kim, H. J. Ahn, H. W. Seol, Y. Y. Kim, Y. B. Park, C. J. Yoon, D. W. Kim, S. H. Kim, and S. Y. Moon. 2005. Derivation and characterization of new human embryonic stem cell lines: SNUhES1, SNUhES2, and SNUhES3. Stem Cells. 23:211-9.

Panopoulos, A. D., O. Yanes, S. Ruiz, Y. S. Kida, D. Diep, R. Tautenhahn, A. Herrerias, E. M. Batchelder, N. Plongthongkum, M. Lutz, W. T. Berggren, K. Zhang, R. M. Evans, G. Siuzdak, and J. C. Izpisua Belmonte. 2012. The metabolome of induced pluripotent stem cells reveals metabolic changes occurring in somatic cell reprogramming. Cell Res. 22:168-77.

Son, M. J., B. R. Jeong, Y. Kwon, and Y. S. Cho. 2013. Interference with the mitochondrial bioenergetics fuels reprogramming to pluripotency via facilitation of the glycolytic transition. Int J Biochem Cell Biol. 45:2512-8.

St John, J. C., J. Ramalho-Santos, H. L. Gray, P. Petrosko, V. Y. Rawe, C. S. Navara, C. R. Simerly, and G. P. Schatten. 2005. The expression of mitochondrial DNA transcription factors during early cardiomyocyte in vitro differentiation from human embryonic stem cells. Cloning Stem Cells. 7:141-53.

Takahashi, K., K. Tanabe, M. Ohnuki, M. Narita, T. Ichisaka, K. Tomoda, and S. Yamanaka. 2007. Induction of pluripotent stem cells from adult human fibroblasts by defined factors. Cell. 131:861-72.

Takahashi, K., and S. Yamanaka. 2006. Induction of pluripotent stem cells from mouse embryonic and adult fibroblast cultures by defined factors. Cell. 126:663-76.

Varum, S., O. Momcilovic, C. Castro, A. Ben-Yehudah, J. Ramalho-Santos, and C. S. Navara. 2009. Enhancement of human embryonic stem cell pluripotency through inhibition of the mitochondrial respiratory chain. Stem Cell Res. 3:142-56.

Varum, S., A. S. Rodrigues, M. B. Moura, O. Momcilovic, C. A. t. Easley, J. Ramalho-Santos, B. Van Houten, and G. Schatten. 2011. Energy metabolism in human pluripotent stem cells and their differentiated counterparts. PLoS One. 6:e20914.

Zhou, W., M. Choi, D. Margineantu, L. Margaretha, J. Hesson, C. Cavanaugh, C. A. Blau, M. S. Horwitz, D. Hockenbery, C. Ware, and H. Ruohola-Baker. 2012. HIF1alpha induced switch from bivalent to exclusively glycolytic metabolism during ESC-to-EpiSC/hESC transition. EMBO J. 31:2103-16.

What is claimed is:

1. A method for preparing pluripotent stem cells, comprising culturing said pluripotent stem cells under ambient oxygen conditions in a culture medium comprising one or more compounds selected from the group consisting of: 5-[(3R or 3S)-dithiolan-3-yl]pentanoic acid ("compound 3"), 5-methylthiazole ("compound 4"), 3-methyl-4-phenyl-1H-imidazole-2-thione ("compound 5"), ethyl 2-(1H-tetrazol-5-yl)acetate ("compound 6"), 5-aminotetrazole ("compound 7"), 5-methylsulfanyl-1H-tetrazole ("compound 12"), and salts thereof, wherein pluripotency is maintained during said culturing.

2. The method of claim 1 wherein the one or more compounds are present in the medium between 0.01 mM and 10 mM.

3. The method of claim 1, wherein said culturing occurs under a condition comprising at least one of (a) greater than 72 hours, (b) one cell doubling, or (c) 10 cell passages.

4. The method of claim 1, wherein the cells in culture are human cells selected from the group consisting of: embryonic stem cells, modified hES cell lines, induced pluripotent stem (iPS) cell lines, and human progenitor cells.

5. The method of claim 1, further comprising measuring the cells in the culture for expression of one or more genes selected from the group consisting of: NANOG, Octamer-binding protein 4 ("OCT4"), and SURVIVIN.

6. A method for culturing stem cells that are human embryonic stem cells (hESCs), pluripotent stem cells, or induced pluripotent stem cells, comprising:

culturing the stem cells on a feeder layer in a culture medium comprising one or more compounds selected from the group consisting of: 5-[(3R or 3S)-dithiolan-3-yl]pentanoic acid ("compound 3"), 5-methylthiazole ("compound 4"), 3-methyl-4-phenyl-1H-imidazole-2-thione ("compound 5"), ethyl 2-(1H-tetrazol-5-yl)acetate ("compound 6"), 5-aminotetrazole ("compound 7"), 5-methylsulfanyl-1H-tetrazole ("compound 12"), and salts thereof, under ambient oxygen conditions.

7. The method of claim 6 further comprising the step of cryopreserving the cells after culture.

8. The method of claim 1, wherein the one or more compounds comprises 5-[(3R or 3S)-dithiolan-3-yl]pentanoic acid ("compound 3") or a salt thereof.

9. The method of claim 1, wherein the one or more compounds comprises 5-methylthiazole ("compound 4") or a salt thereof.

10. The method of claim 1, wherein the one or more compounds comprises 3-methyl-4-phenyl-1H-imidazole-2-thione ("compound 5") or a salt thereof.

11. The method of claim 1, wherein the one or more compounds comprises ethyl 2-(1H-tetrazol-5-yl)acetate ("compound 6") or a salt thereof.

12. The method of claim 1, wherein the one or more compounds comprises 5-aminotetrazole ("compound 7") or a salt thereof.

13. The method of claim 1, wherein the one or more compounds comprises 5-methylsulfanyl-1H-tetrazole ("compound 12") or a salt thereof.

14. The method of claim 1, wherein the pluripotent stem cells are human pluripotent stem cells.

15. The method of claim 6, wherein the one or more compounds comprises 5-aminotetrazole ("compound 7") or a salt thereof.

16. A composition comprising:
a mammalian stem cell culture medium;
a growth factor; and
an effective amount of 5-aminotetrazole ("compound 7") or a salt thereof.

17. The composition of claim 16, wherein the growth factor is basic fibroblast growth factor (bFGF).

18. A kit comprising:
a mammalian stem cell culture medium comprising a growth factor; and
an effective amount of 5-aminotetrazole ("compound 7") or a salt thereof.

19. The kit of claim 18, wherein the mammalian stem cell culture medium and the 5-aminotetrazole ("compound 7") or salt thereof are present in separate containers.

20. The kit of claim 18, wherein the mammalian stem cell culture medium comprises the 5-aminotetrazole ("compound 7") or salt thereof.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 1
cgaggctggc ttcatcca                                           18

<210> SEQ ID NO 2
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 2
gcaaccggac gaatgcttt                                          19

<210> SEQ ID NO 3
<211> LENGTH: 18
<212> TYPE: DNA
<213> ORGANISM: Artificial sequence
<220> FEATURE:
<223> OTHER INFORMATION: Synthetic nucleic acid sequence

<400> SEQUENCE: 3
accccataga ggaacata                                           18
```